US006375950B1

(12) United States Patent
Noelle et al.

(10) Patent No.: US 6,375,950 B1
(45) Date of Patent: *Apr. 23, 2002

(54) METHODS FOR INDUCING T CELL UNRESPONSIVENESS TO DONOR TISSUE OR ORGAN IN A RECIPIENT WITH GP39 ANTAGONISTS

(75) Inventors: Randolph J. Noelle, Cornish, NH (US); Fiona H. Durie, Seattle, WA (US)

(73) Assignees: University of Massachusetts Medical Center, Worcester, MA (US); Trustees of Dartmouth College, Hanover, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/227,081

(22) Filed: Jan. 5, 1999

Related U.S. Application Data

(62) Division of application No. 08/906,332, filed on Aug. 5, 1997, now Pat. No. 5,902,585, which is a division of application No. 08/234,987, filed on Apr. 27, 1994, now Pat. No. 5,683,693.

(51) Int. Cl.$^7$ ...................... A61K 39/395; A61K 39/00; C07K 16/28; C07K 16/46; C07K 14/705

(52) U.S. Cl. ................... 424/154.1; 424/130.1; 424/133.1; 424/134.1; 424/141.1; 424/143.1; 424/144.1; 424/153.1; 424/173.1; 424/184.1; 424/93.7; 424/93.71; 424/577; 424/192.1; 514/2; 514/8; 514/885; 530/387.1; 530/387.3; 530/388.1; 530/388.2; 530/388.22; 530/388.7; 530/388.73; 530/388.75; 530/350

(58) Field of Search ............. 424/130.1, 133.1, 424/143.1, 173.1, 93.7, 192.1, 134.1, 144.1, 184.1, 93.71, 141.1, 154.1, 153.1, 577; 514/2, 8, 885; 530/387.1, 388.2, 388.73, 350, 387.3, 388.22, 388.75, 388.1, 388.7

(56) References Cited

U.S. PATENT DOCUMENTS

| 5,474,771 A |   | 12/1995 | Lederman .................. 424/133 |
| 5,683,693 A | * | 11/1997 | Noelle et al. |
| 5,869,049 A | * | 2/1999  | Noelle et al. |
| 5,876,718 A | * | 3/1999  | Noelle et al. |
| 5,902,585 A | * | 5/1999  | Noelle et al. |
| 5,942,229 A | * | 8/1999  | Noelle et al. |

FOREIGN PATENT DOCUMENTS

| EP | 0555880    | 8/1993 |
| EP | 0585943    | 3/1994 |
| WO | WO93/08207 | 4/1993 |
| WO | WO93/09812 | 5/1993 |
| WO | WO94/04570 | 3/1994 |

OTHER PUBLICATIONS

Auchincloss in Transplantation Immunology. Bach and Auchincloss (Eds.) Wiley–Liss, NY 1995 pp. 211–218.*
Tisch PNAS 91: 437–438 (1994).*
Stuber et al. J Exp Med 183: 693–698 (1996).*
Illustrated Dictionary of Immunology. Cruse and Lewis (Eds) CRC Press Boca Raton 1995. pp. 297–298.*
Markees et al., Transplant Proc. 28:814–815 (1996).
Gerritse et al., PNAS 93:2499–2504 (1996).
Tisch et al., PNAS 91:437–438 (1994).
Sharkey et al., Cancer Res. (Suppl) 55:59355 (1995).
Larsen et al., Transplantation 61:4–9 (1996).
Rossini et al., Cell Transplantation 5:49–52 (1996).
Bhatia et al., 9th Intl. Congress of Immunology, San Francisco, CA, USA, p. 311, (1995).
Pulito et al., J. Immunol., 150:2840–2850 (1996), p. 2840 only.
Durie, F., et al., "Allogeneic Tolerance Induced by Treatment with an Antibody to the Ligand for CD40,", *FASEB Journal,* Abstracts Part 1, Ab. No. 2763, vol. 8, No. 4, p. a477. (1994).
Monaco, Immunomethods 2:159–170 (1993).
Wee et al. Transplantation 58:261–264 (1994).
Paul et al. Fundamental Immunology Raven Press p. 242 Only (1993).
Marshall et al. J. Clin. Immunology 3(3) :165–173 (1993).
Clark and Ledbetter, (1994) "How B and T Cells . . . other", *Nature,* 367:425–428.
Aruffo, et al., (1993) "The CD40 ligand . . . Hyper–IgM Syndrome", *Cell,* 72:291–300.
Korthauer, et al. (1993) "Deffective expression . . . hyper–IgM" *Nature* 361:539–541.

(List continued on next page.)

*Primary Examiner*—Phillip Gambel
(74) *Attorney, Agent, or Firm*—Robin L. Teskin

(57) ABSTRACT

Methods for inducing T cell tolerance to a tissue or organ graft in a transplant recipeint are disclosed. The methods involve administering to a subject: 1) an allogeneic or xenogeneic cell which expresses donor antigens and which has a ligand on the cell surface which interacts with a receptor on the surface of a recipient T cell which mediates contact-dependent helper effector function; and 2) an antagonist of the receptor which inhibits interaction of the ligand with the receptor. In a preferred embodiment, the allogeneic or xenogeneic cell is a B cell, preferably a resting B cell, and the molecule on the surface of the T cell which mediates contact-dependent helper effector function is gp39. A preferred gp39 antagonist is an anti-gp39 antibody. The allogeneic or xenogeneic cell and the gp39 antagonist are typically administered to a transplant recipient prior to transplantation of the tissue or organ. The methods of the invention can be used to induce T cell tolerance to transplants such as liver, kidney, heart, lung, skin, muscle, neuronal tissue, stomach and intestine. A method for treating diabetes comprising administering to a subject allogeneic or xenogeneic cells expressing donor antigens, a gp39 antagonist and pancreatic islets is also disclosed.

7 Claims, 7 Drawing Sheets

OTHER PUBLICATIONS

DiSanto, et al., (1993) "CD40 ligand mutations . . . hyper–IgM" *Science* 259:541–543.

Allen, et al., (1993) "CD40 ligand . . . Syndrome". *Science* 259:990–993.

Ranheim, et al. (1993) "Activated T cells . . . signal" *J. Exp. Med.* 177:925–935.

Foy, et al. (1993) "In Vivo . . . gp39" *J. Exp. Med.* 178:1567–1575.

Lin, et al. (1993) "Long–Term Acceptance . . . Transfusion" *J. Exp. Med.* 178:1801–1806.

Harris (1993) "Therapeutic antibodies . . . age" *TIBTECH* 11:42–44.

Noelle et al. (1992) "A 39–kDa protein . . . B cells" *Proc. Natl. Acad. Sci. USA* 89:6550–6554.

Noelle et al. (1992) "CD40 and . . . activation" *Immun. Today* 13:431–433.

Hollenbaugh et al. (1992) "The human T cell . . . activity" *EMBO Journal* 11:4313–4321.

Armitage et al. (1992) "Molecular . . . CD40" *Nature* 357:80–82.

Lane et al. (1992) Activated human . . . lymphocytes *Eur. J. Immuno.* 22:2573–2578.

Lederman et al. (1992) "Identification of a . . . (Help)" *J. Exp. Med.* 175:1091–1101.

Spriggs et al. (1992) "Recombinant Human . . . E secretion" *J. Exp. Med.* 176:1543–1550.

Lederman et al. (1992) "Molecular interactions . . . follicles" *J. Immuno.* 149(12):3817–3826.

Fanslow et al. (1992) "Soluble forms of CD40 . . . B cells" *J. Immuno.* 149:655–660.

Eynon and Parker, (1992) "Small B Cells . . . Antigen" *J. Exp. Med.* 175:131–138.

Linsley et al. (1992) "Immunosuppression in Vivo . . . Molecule" *Science* 257:792–795.

Lenschow et al. (1992) "Long–term Survival . . . CTLA4Ig" *Science* 257:789–790.

Turka et al. (1992) "T–cell . . . in vivo" *Proc. Natl. Acad. Sci. USA* 89:11102–11105.

Waldmann (1992) "Immune Receptors . . . Rejection" *Annu. Rev. Immuno.* 10:675–704.

Noelle and Snow (1992) "T helper Cells" *Curr. Op. Immuno.* 4:333–337.

Yellin et al. (1991) "A huan CD4–T cell . . . function" *J. Immuno.* 147:3389–3395.

Waldmann et al. (1991) "Monoclonal . . . therapy" *Science* 52:1657–1662.

Bartlett et al. (1990) "Cognate interactions . . . B Cells" *J. Immuno.* 145(12):3956–3962.

Hodgkin et al. (1990) "Separation of . . . lymphokines" *J. Immuno.* 145(7):2025–2034.

Aruffo et al. (1990) "CD44 is the . . . Hyaluronate" *Cell* 61:1303–1313.

Stamenkovic et al. (1989) "A B–lymphocyte . . . carcinomas" *The EMBO J.* 8(5):1403–1410.

Paulie et al. (1989) "The human B . . . transduction" *J. Immuno.* 142:590–595.

Sharabi et al. (1989) "Mixed chimerism and . . . regimen" *J. Exp. Med.* 169:493–502.

Dillman (1989) "Monoclonal . . . Cancer" *Annals Inter. Med.* 111(7):592–603.

Waldmann (1989) "Manipulation . . . Antibodies" *Annu. Rev. Immuno.* 7:407–444.

Cobboid et al. (1986) "Monoclonal . . . tolerance" *Nature* 323:164–166.

* cited by examiner

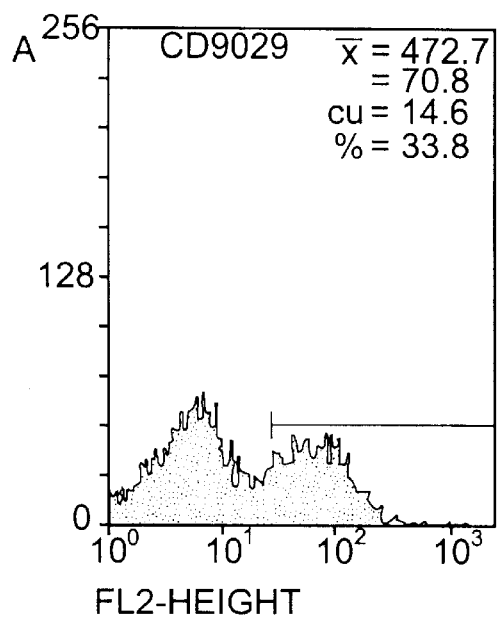
FIG. 3A
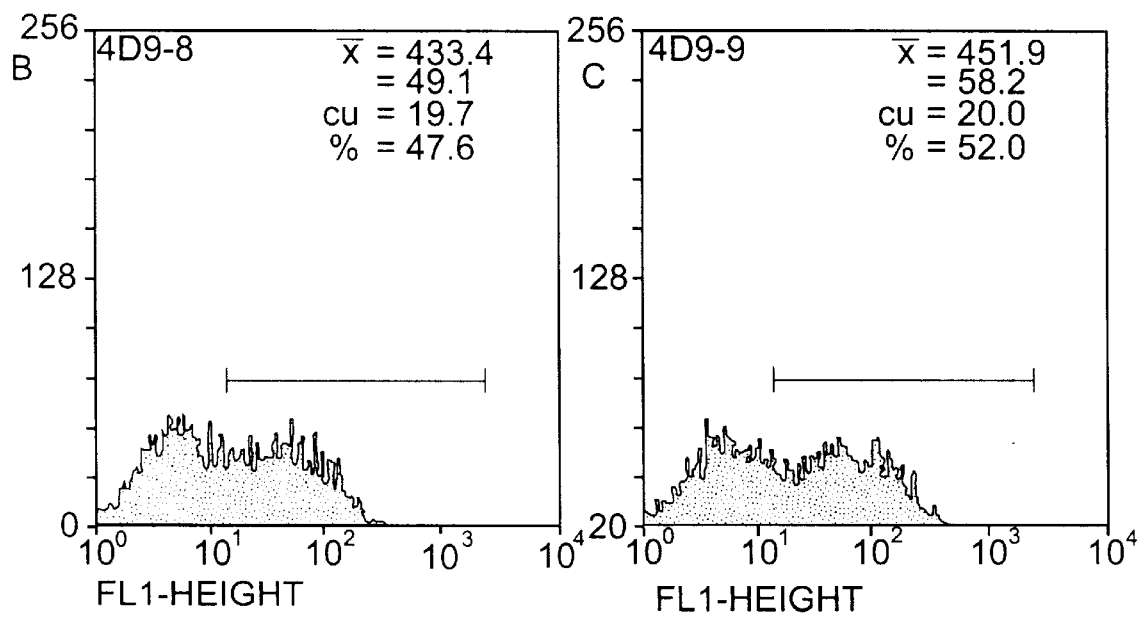
FIG. 3B  FIG. 3C

METHODS FOR INDUCING T CELL UNRESPONSIVENESS TO DONOR TISSUE OR ORGAN IN A RECIPIENT WITH GP39 ANTAGONISTS

This application is a divisional of application Ser. No. 08/906,332, filed Aug. 5, 1997, now U.S. Pat. No. 5,902,585 which in turn is a divisional of application Ser. No. 08/234,987, filed Apr. 25, 1994, now U.S. Pat. No. 5,683,693 the contents of which are incorporated herein by reference.

GOVERNMENT FUNDING

The work leading to this invention was supported in part by National Institutes of Health grants AI29544, DK41235, DK25306, DK36024, and AI26296. The U.S. government therefore may have certain rights in this invention.

BACKGROUND OF THE INVENTION

To induce antigen-specific T cell activation and clonal expansion, two signals provided by antigen-presenting cells (APCs) must be delivered to the surface of resting T lymphocytes (Jenkins, M. and Schwartz, R. (1987) *J. Exp. Med* 165, 302–319; Mueller, D. L., et al. (1990) *J. Immunol.* 144, 3701–3709; Williams, I. R. and Unanue, E. R. (1990) *J. Immunol.* 145, 85–93). The first signal, which confers specificity to the immune response, is mediated via the T cell receptor (TCR) following recognition of foreign antigenic peptide presented in the context of the major histocompatibility complex (MHC). The second signal, termed costimulation, induces T cells to proliferate and become functional (Schwartz, R. H. (1990) *Science* 248, 1349–1356). Costimulation is neither antigen-specific, nor MHC restricted and is thought to be provided by one or more distinct cell surface molecules expressed by APCs (Jenkins, M. K., et al. (1988) *J. Immunol.* 140, 3324–3330; Linsley, P. S., et al. (1991) *J. Exp. Med.* 173, 721–730; Gimmi, C. D., et al., (1991) *Proc. Natl. Acad. Sci. USA.* 88, 6575–6579; Young, J. W., et al. (1992) *J. Clin. Invest.* 90, 229–237; Koulova, L., et al. (1991) *J. Exp. Med.* 173, 759–762; Reiser, H., et al. (1992) *Proc. Natl. Acad. Sci. USA.* 89, 271–275; van-Seventer, G. A., et al. (1990) *J. Immunol.* 144, 4579–4586; LaSalle, J. M., et al., (1991) *J. Immunol.* 147, 774–80; Dustin, M. I., et al., (1989) *J. Exp. Med.* 169, 503; Armitage, R. J., et al. (1992) *Nature* 357, 80–82; Liu, Y., et al. (1992) *J. Exp. Med.* 175, 437–445). One costimulatory pathway involved in T cell activation involves the molecule CD28 on the surface of T cells. This molecule can receive a costimulatory signal delivered by a ligand on B cells or other APCs. Ligands for CD28 include members of the B7 family of B lymphocyte activation antigens such as B7-1 and/or B7-2 (Freedman. A. S. et al. (1987) *J. Immunol.* 137, 3260–3267; Freeman, G. J. et al. (1989) *J. Immunol.* 143, 2714–2722; Freeman, G. J. et al. (1991) *J. Exp. Med.* 174, 625–631; Freeman, G. J. et al (1993) *Science* 262, 909–911; Azuma, M. et al. (1993) *Nature* 366, 76–79; Freeman, G. J. et al. (1993) *J. Exp. Med.* 178, 2185–2192). B7-1 and B7-2 are also ligands for another molecule, CTLA4, present on the surface of activated T cells, although the role of CTLA4 in costimulation is unclear.

Delivery to a T cell of an antigen-specific signal with a costimulatory signal leads to T cell activation, which can include both T cell proliferation and cytokine secretion. In contrast, delivery to a T cell of an antigen-specific signal in the absence of a costimulatory signal is thought to induce a state of unresponsiveness or anergy in the T cell, thereby inducing antigen-specific tolerance in the T cell.

Interactions between T cells and B cells play a central role in immune responses. Induction of humoral immunity to thymus-dependent antigens requires "help" provided by T helper (hereafter Th) cells. While some help provided to B lymphocytes is mediated by soluble molecules released by Th cells (for instance lymphokines such as IL-4 and IL-5), activation of B cells also requires a contact-dependent interaction between B cells and Th cells. Hirohata et al., *J. Immunol.*, 140:3736–3744 (1988); Bartlett et al., *J. Immunol.*, 143:1745–1754 (1989). This indicates that B cell activation involves an obligatory interaction between cell surface molecules on B cells and Th cells. The molecule(s) on the T cell therefore mediates contact-dependent helper effector functions of the T cell. A contact-dependent interaction between molecules on B cells and T cells is further supported by the observation that isolated plasma membranes of activated T cells can provide helper functions necessary for B cell activation. Brian, *Proc. Natl. Acad Sci. USA,* 85:564–568 (1988); Hodgkin et al., *J. Immunol.,* 145:2025–2034 (1990); Noelle et al., *J. Immunol.,* 146:1118–1124 (1991).

A molecule, CD40, has been identified on the surface of immature and mature B lymphocytes which, when crosslinked by antibodies, induces B cell proliferation. Valle et al., *Eur. J. Immunol.,* 19:1463–1467 (1989); Gordon et al., *J. Immunol.,* 140:1425–1430 (1988); Gruber et al., *J. Immunol.,* 142: 4144–4152 (1989). CD40 has been molecularly cloned and characterized. Stamenkovic et al., *EMBO J.,* 8:1403–1410 (1989). A ligand for CD40, gp39 (also called CD40 ligand or CD40L) has also been molecularly cloned and characterized. Armitage et al., *Nature,* 357:80–82 (1992); Lederman et al., *J. Exp. Med.,* 175:1091–1101 (1992); Hollenbaugh et al, *EMBO J.,* 11:4313–4319 (1992). The gp39 protein is expressed on activated, but not resting, $CD4^+$ Th cells. Spriggs et al., *J. Exp. Med.,* 176:1543–1550 (1992); Lane et al., *Eur. J. Immunol.,* 22:2573–2578 (1992); Roy et al., *J. Immunol.,* 151:1–14 (1993). Cells tansfected with the gp39 gene and expressing the gp39 protein on their surface can trigger B cell proliferation and, together with other stimulatory signals, can induce antibody production. Armitage et al., *Nature,* 357:80–82 (1992); Hollenbaugh et al., *EMBO J.,* 11:4313–4319 (1992).

SUMMARY OF THE INVENTION

Cell-surface molecules which mediate contact-dependent helper effector functions of T cells are important for inducing immune responses which require T cell help. For example, the interaction of gp39 on T cells with CD40 on B cells plays a central role in activating B cell responses to an antigen. The current invention is based, at least in part, on the discovery that cell-surface molecules which mediate contact-dependent helper effector functions of T cells also play a critical role in the response of T cells to alloantigens. In particular, it has been discovered that, under appropriate conditions, interference with an interaction of gp39 with a ligand on an allogeneic cell which is presenting alloantigens to the T cell can induce tolerance in the T cell. Preferably, the allogeneic cell which presents alloantigens to the T cell requires an interaction between a gp39 ligand on the cell and gp39 on the T cell to be able to provide signals necessary for activation of the T cell. Inhibiting the interaction of the gp39 ligand on the allogeneic cell with gp39 on the T cell prevents T cell activation and rather induces alloantigen-specific T cell tolerance. Induction of T cell tolerance to alloantigens as described herein can be used as a preparative regimen for tissue or organ transplantation.

Accordingly, the methods of the invention are particularly useful for inducing T cell tolerance to a donor tissue or organ in a recipient of the tissue or organ The methods involve administering to a transplant recipient: 1) an allogeneic or xenogeneic cell which expresses at least one donor antigen and which has a ligand on a cell surface which interacts with a receptor on the surface of a recipient T cell which mediates contact-dependent helper effector functions; and 2) an antagonist of the molecule on the surface of the recipient T cell which mediates contact-dependent helper effector functions. The antagonist inhibits an interaction between the molecule on the T cell and it's ligand on the allogeneic or xenogeneic cell.

In a preferred embodiment, the receptor on the surface of a recipient T cell which mediates contact-dependent helper effector functions is gp39. In this embodiment, the antagonist is a molecule which inhibits the interaction of gp39 on a T cell with a gp39 ligand on an allogeneic or xenogeneic cell. A particularly preferred gp39 antagonist is an anti-gp39 antibody. In another embodiment, the gp39 antagonist is a soluble form of a gp39 ligand, for example soluble CD40. The allogeneic or xenogeneic cell which is administered to the recipient is preferably a lymphoid cell, for example a B cell. Alternatively, the allogeneic or xenogeneic cell is a small resting B cell. The allogeneic or xenogeneic cell and the antagonist (e.g., anti-gp39 antibody) are typically administered to a recipient subject prior to transplantation of the tissue or organ into the subject For example, lymphoid cells (e.g., B cells) from the donor of the tissue or organ are administered to the recipient, together with the antagonist, prior to transplantation of the tissue or organ into the recipient.

The methods of the current invention can be used, for example, to induce T cell tolerance to transplanted tissue or organs such as liver, kidney, heart, lung, skin, muscle, neuronal tissue, stomach and intestines. In one embodiment, the transplanted tissue comprises pancreatic islets. Accordingly, the invention provides a method for treating diabetes comprising administering to a subject in need of treatment: 1) allogeneic or xenogeneic cells which express donor antigens; 2) an antagonist of a receptor on the surface of recipient T cells which mediates contact-dependent helper effector functions, such as a gp39 antagonist (e.g., an anti-gp39 antibody); and 3) donor pancreatic islets.

BRIEF DESCRIPTION OF THE DRAWINGS

FIGS. 3A, 3B and 3C are flow cytometic profiles depicting the staining of 6 hour activated human peripheral blood lymphocytes with either CD40Ig (panel A), mAb 4D9-8 (panel B) or mAb 4D9-9 (panel C).

DETAILED DESCRIPTION OF THE INVENTION

Figure 1:
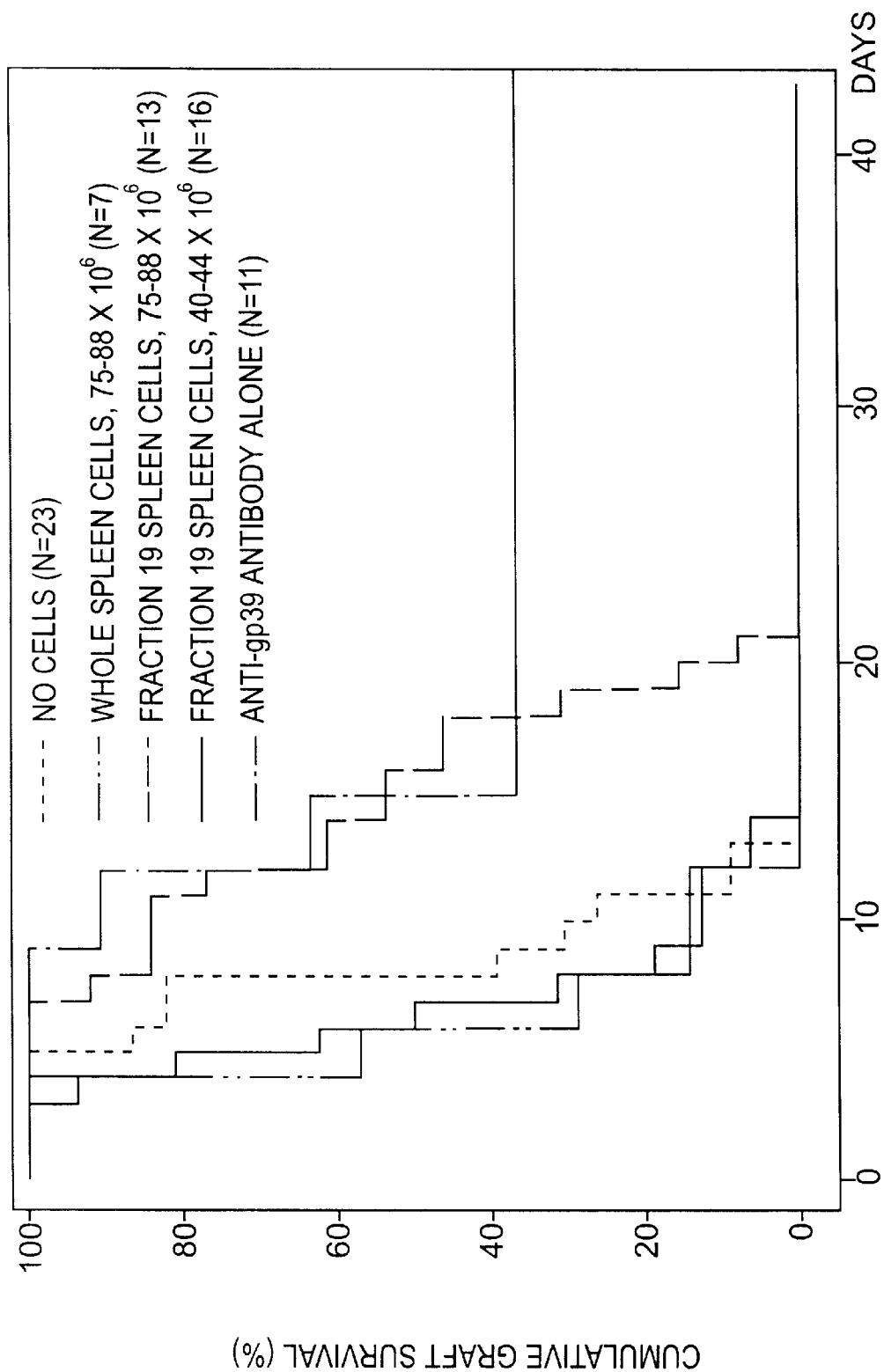
FIG. 1 is a graphic representation of the survival of transplanted pancreatic islet allografts in chemically diabetic mice pretreated with anti-gp39 antibody alone or pretreated with unfractionated or fractionated allogeneic spleen cells alone.

This invention features methods for inducing T cell tolerance in vivo to a donor tissue or organ transplant in a transplant recipient. The methods involve administering to the recipient 1) an allogeneic or xenogeneic cell which expresses donor antigens and which has a ligand on a cell surface which interacts with a receptor on the surface of a recipient T cell which mediates contact-dependent helper effector function, and 2) an antagonist of the receptor on the surface of the T cell which inhibits interaction of the ligand and the receptor. As used herein the term "recipient" refers to a subject into whom a tissue or organ graft is to be transplanted, is being transplanted or has been transplanted. As defined herein, an "allogeneic" cell is obtained from a different individual of the same species as the recipient and expresses "alloantigens", which differ from antigens expressed by cells of the recipient. A "xenogeneic" cell is obtained from a different species than the recipient and expresses "xenoantigens", which differ from antigens expressed by cells of the recipient. As used herein, the term "donor antigens" refers to antigens expressed by the donor tissue or organ graft to be transplanted into the recipient The donor antigens may be alloantigens or xenoantigens, depending upon the source of the graft. The allogeneic or xenogeneic cell administered to the recipient as part of the tolerization regimen expresses donor antigens, i.e., expresses some or all of the same antigens present on the donor tissue or organ to be transplanted. The allogeneic or xenogeneic cell is preferably obtained from the donor of the tissue or organ graft but can be obtained from one or more sources having common antigenic determinants with the donor.

In addition to the allogeneic or xenogeneic cell, an antagonist of a molecule on T cells which mediates contact dependent helper effector functions is administered to the recipient as part of the tolerization regimen. As defined herein, a molecule or receptor which mediates contact dependent helper effector functions is one which is expressed on a Th cell and interacts with a ligand on an effector cell (e.g., a B cell), wherein the interaction of the molecule with it's ligand is necessary for generation of an effector cell response (e.g., B cell activation). In addition to being involved in effector cell responses, it has now been found that such a molecule or receptor is involved in the response of the T cell to antigen. Preferably, the molecule on a T cell which mediates contact-dependent helper effector function is gp39. Accordingly, in preferred embodiments, the methods of the invention involve administering to a transplant recipient an allogeneic or xenogeneic cell and a gp39 antagonist. Activation of recipient T cells by the allogeneic or xenogeneic cell involves an interaction between gp39 on recipient T cells and a gp39 ligand on the allogeneic or xenogeneic cell. By inhibiting this interaction with a gp39 antagonist, the T cells of the recipient are not activated by the donor antigens expressed by the allogeneic or xenogeneic cell but rather become tolerized to the donor antigens. Induction of tolerance to donor antigens in the recipient thus enables successful transplantation of the donor tissue or organ without immune-mediated rejection of the donor graft.

Various aspects of the invention are described in further detail in the following subsections.

I. gp39 Antagonists

According to the methods of the invention, a gp39 antagonist is administered to a recipient to interfere with the interaction of gp39 on recipient T cells with a gp39 ligand on an allogeneic or xenogeneic cell, such as a B cell, administered to the recipient. A gp39 antagonist is defined as a molecule which interferes with this interaction. The gp39 antagonist can be an antibody directed against gp39 (e.g, a monoclonal antibody against gp39 ), a fragment or derivative of an antibody directed against gp39 (e.g., Fab or F(ab)'2 fragments, chimeric antibodies or humanized antibodies), soluble forms of a gp39 ligand (e.g., soluble CD40), soluble forms of a fusion protein of a gp39 ligand (e.g., soluble CD40Ig), or pharmaceutical agents which disrupt or interfere with the gp39-CD40 interaction.

A. Antibodies

A mammal, (e.g., a mouse, hamster, or rabbit) can be immunized with an immunogenic form of gp39 protein or protein fragment (e.g., peptide fragment) which elicits an antibody response in the mammal. A cell which expresses gp39 on its surface can also be used as the immunogen. Alternative immunogens include purified gp39 protein or protein fragments. gp39 can be purified from a gp39-expressing cell by standard purification techniques. Additionally, gp39 cDNA (Armitage et al., *Nature,* 357:80–82 (1992); Lederman et al., *J. Exp. Med.,* 175:1091–1101 (1992); Hollenbaugh et al., *EMBO J.,* 11:4313–4319 (1992)) can be expressed in a host cell, e.g., bacteria or a mammalian cell line, and gp39 protein purified from cell cultures by standard techniques. Alternatively, gp39 peptides can be synthesized based upon the amino acid sequence of gp39 (disclosed in Armitage et al., *Nature,* 357:80–82 (1992); Lederman et al., *J. Exp. Med.,* 175:1091–1101 (1992); Hollenbaugh et al., *EMBO J.,* 11:4313–4319 (1992)) using known techniques (e.g. F-moc or T-boc chemical synthesis). Techniques for conferring immunogenicity on a protein include conjugation to carriers or other techniques well known in the art. For example, the protein can be administered in the presence of adjuvant. The progress of immunization can be monitored by detection of antibody titers in plasma or serum. Standard ELISA or other immunoassay can be used with the immunogen as antigen to assess the levels of antibodies.

Following immunization, antisera can be obtained and, if desired, polyclonal antibodies isolated from the sera. To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art. For example, the hybridoma technique originally developed by Kohler and Milstein (*Nature* (1975) 256:495–497) as well as other techniques such as the human B-cell hybridoma technique (Kozbar et al., *Immunol. Today* (1983) 4:72), the EBV-hybridoma technique to produce human monoclonal antibodies (Cole et al. *Monoclonal Antibodies in Cancer Therapy* (1985) (Allen R. Bliss, Inc., pages 77–96), and screening of combinatorial antibody libraries (Huse et al., *Science* (1989) 246:1275). Hybridoma cells can be screened immunochemically for production of antibodies specifically reactive with the protein or peptide and monoclonal antibodies isolated.

The term antibody as used herein is intended to include fragments thereof which are specifically reactive with a gp39 protein or peptide thereof or gp39 fusion protein. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. The antibody of the invention is further intended to include bispecific and chimeric molecules having an anti-gp39 portion.

When antibodies produced in non-human subjects are used therapeutically in humans, they are recognized to varying degrees as foreign and an immune response may be generated in the patient. One approach for minimizing or eliminating this problem, which is preferable to general immunosuppression, is to produce chimeric antibody derivatives, i.e., antibody molecules that combine a non-human animal variable region and a human constant region. Chimeric antibody molecules can include, for example, the antigen binding domain from an antibody of a mouse, rat, or other species, with human constant regions. A variety of approaches for making chimeric antibodies have been described and can be used to make chimeric antibodies containing the immunoglobulin variable region which recognizes gp39. See, for example, Morrison et al., *Proc. Natl. Acad. Sci. U.S.A.* 81:6851 (1985); Takeda et al., *Nature* 314:452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B. It is expected that such chimeric antibodies would be less immunogenic in a human subject than the corresponding non-chimeric antibody.

For human therapeutic purposes the monoclonal or chimeric antibodies specifically reactive with a gp39 protein or peptide can be further humanized by producing human variable region chimeras, in which parts of the variable regions, especially the conserved framework regions of the antigen-binding domain, are of human origin and only the hypervariable regions are of non-human origin. Such altered immunoglobulin molecules may be made by any of several techniques known in the art, (e.g., Teng et al., *Proc. Natl. Acad. Sci. U.S.A.,* 80:7308–7312 (1983); Kozbor et al., *Immunology Today,* 4:7279 (1983); Olsson et al., *Meth. Enzymol.,* 92:3–16 (1982)), and are preferably made according to the teachings of PCT Publication WO92/06193 or EP 0239400. Humanized antibodies can be commercially produced by, for example, Scotgen Limited, 2 Holly Road, Twickenham, Middlesex, Great Britain.

Another method of generating specific antibodies, or antibody fragments, reactive against a gp39 protein or peptide is to screen expression libraries encoding immunoglobulin genes, or portions thereof, expressed in bacteria with a gp39 protein or peptide. For example, complete Fab fragments, VH regions and FV regions can be expressed in bacteria using phage expression libraries. See for example Ward et al., *Nature,* 341: 544–546: (1989); Huse et al.,

*Science*, 246: 1275–1281 (1989); and McCafferty et al., *Nature*, 348: 552–554 (1990). Screening such libraries with, for example, a gp39 peptide can identify immunoglobin fragments reactive with gp39. Alternatively, the SCID-hu mouse (available from Genpharm) can be used to produce antibodies, or fragments thereof.

Methodologies for producing monoclonal antibodies directed against gp39, including human $gp^{39}$ and mouse gp39, and suitable monoclonal antibodies for use in the methods of the invention, are described in further detail in Example 2.

B. Soluble Ligands for gp39

Other gp39 antagonists which can be administered to induce T cell tolerance include soluble forms of a gp39 ligand. A monovalent soluble ligand of gp39, such as soluble CD40, can bind to gp39, thereby inhibiting the interaction of gp39 with CD40 on B cells. The term "soluble" indicates that the ligand is not permanently associated with a cell membrane. A soluble gp39 ligand can be prepared by chemical synthesis, or, preferably by recombinant DNA techniques, for example by expressing only the extracellular domain (absent the transmembrane and cytoplasmic domains) of the ligand. A preferred soluble gp39 ligand is soluble CD40. Alternatively, a soluble gp39 ligand can be in the form of a fusion protein. Such a fusion protein comprises at least a portion of the gp39 ligand attached to a second molecule. For example, CD40 can be expressed as a fusion protein with immunoglobulin (i.e., a CD40Ig fusion protein). In one embodiment, a fusion protein is produced comprising amino acid residues of an extracellular domain portion of CD40 joined to amino acid residues of a sequence corresponding to the hinge, CH2 and CH3 regions of an immunoglobulin heavy chain, e.g. Cγ1, to form a CD40Ig fusion protein (see e.g., Linsley et al. (1991) *J. Exp. Med.* 1783:721–730; Capon et al. (1989) *Nature* 337, 525–531; and Capon U.S. Pat. No. 5,116,964). The fusion protein can be produced by chemical synthesis, or, preferably by recombinant DNA techniques based on the cDNA of CD40 (Stamenkovic et al., *EMBO J.*, 8:1403–1410 (1989)).

II. Cells for Induction of Antigen-Specific Tolerance

The current invention is based, at least in part, on the discovery that presentation of alloantigens to T cells by allogeneic cells in the presence of a gp39 antagonist results in T cell tolerance to the alloantigens. Cells which are capable of inducing tolerance by this mechanism include those which present antigen and activate T cells by interaction with gp39 (i.e. an interaction between gp39 on T cells and a gp39 ligand on the cell presenting antigen is necessary to deliver the appropriate signals for T cell activation to the T cell). Inhibition of the interaction of the ligand on the allogeneic or xenogeneic cell with gp39 on recipient T cells prevents T cell activation by allo- or xenoantigens and, rather, induces T cell tolerance to the antigens. Interference with activation of the T cell via gp39 may prevent the induction of costimulatory molecules on the allogeneic or xenogeneic cell, (e.g. B7 family molecules on a B cell), so that the cell delivers only an antigenic signal to the T cell in the absence of a costimulatory signal, thus inducing tolerance.

Accordingly, in the methods of the invention, an allogeneic or xenogeneic cell is administered to a recipient subject. The allogeneic or xenogeneic cell is capable of antigen to T cells of the recipient, and is, for example, a B lymphocyte, a "professional" antigen presenting cell (e.g., a monocyte, dendritic cell, Langerhan cell) or other cell which presents antigen to immune cells (e.g., a keratinocyte, endothelial cell. astrocyte, fibroblast, oligodendrocyte). Furthermore, it is preferable that the allogeneic or xenogeneic cell has a reduced capacity to stimulate a costimulatory signal in recipient T cells. For example, the allogeneic or xenogeneic cell may lack expression of or express only low levels of costimulatory molecules such as the B7 family of proteins (e.g., B7-1 and B7-2). Expression of costimulatory molecules on potential allogeneic or xenogeneic cells to be used in the method of the invention can be assessed by standard techniques, for example by flow cytometry using antibodies directed against costimulatory molecules.

Preferred allogeneic or xenogeneic cells for inducing T cell tolerance are lymphoid cells, for example peripheral blood lymphocytes or splenic cells. Preferred lymphoid cells for inducing T cell tolerance are B cells. B cells can be purified from a mixed population of cells (e.g., other cell types in peripheral blood or spleen) by standard cell separation techniques. For example, adherent cells can be removed by culturing spleen cells on plastic dishes and recovering the non-adherent cell population. T cells can be removed from a mixed population of cells by treatment with an anti-T cell antibody (e.g., anti-Thy1.1 and/or anti-Thy 1.2) and complement. In one embodiment, resting lymphoid cells, preferably resting B cells, are used as the antigen presenting cells. Resting lymphoid cells, such as resting B cells, can be isolated by techniques known in the art, for example based upon their small size and density. Resting lymphoid cells can be isolated for example by counterflow centrifugal elutriation as described in Example 1. Using counterflow centrifugal elutriation, a small, resting lymphoid cell population depleted of cells which can activate T cell responses can be obtained by collecting a fraction(s) at 14–19 ml/min., preferably 19 ml/min. (at 3,200 rpm). Alternatively, small, resting lymphocytes (e.g., B cells) can be isolated by discontinuous density gradient centrifugation, for example using a Ficoll or Percoll gradient, and a layer containing small, resting lymphocytes can be obtained after centrifugation. Small resting B cells can also be distinguished from activated B cells by assaying for expression of costimulatory molecules, such as B7-1 and/or B7-2, on the surface of activated B cells by standard techniques (e.g. immunofluorescence).

The allogeneic or xenogeneic cells administered to the recipient function, at least in part, to present donor antigens to recipient T cells. Thus, the cells express antigens which are also expressed by the donor tissue or organ. Typically, this can be accomplished by using allogeneic or xenogeneic cells obtained from the donor of the tissue or organ graft. For example, peripheral lymphoid cells, B cells or spleen cells from the tissue or organ donor can be isolated and used in the methods of the invention. Alternatively, allogeneic or xenogeneic cells can be obtained from a source other than the donor of the tissue or organ as long as the cells have antigenic determinants in common with the tissue or organ donor. For example, allogeneic or xenogeneic cells which express (most or all) of the same major histocompatibilty complex antigens as the donor tissue or organ can be used. Thus, allogeneic or xenogeneic cells may be used from a source which is MHC haplotype matched with the donor of the tissue or organ (e.g., a close relative of the graft donor).

III. Administration of Cells and gp39 Antagonists

T cell tolerance to an organ or tissue graft can be induced according to the invention by administration to the transplant recipient of a gp39 antagonist in conjunction with an allogeneic or xenogeneic cell which expresses donor antigens and interacts with recipient T cells via gp39. In a preferred embodiment, the allogeneic or xenogeneic cell and the gp39 antagonist are administered to the recipient simultaneously or contemporaneously. Alternatively, the gp39 antagonist can be administered prior to administering the allogeneic or xenogeneic cells, for example when the antagonist is an antibody with a long half-life. In a preferred embodiment, the antagonist and the allogeneic or xenogeneic cells are admininstered to the recipient prior to transplantation of the organ or tissue into the recipient (i.e., the recipient is pretreated with the antagonist and cells). For example, administration of the allogeneic or xenogeneic cells and antagonist can be performed several days (e.g., five to eight days) prior to tissue or organ transplantation.

Administration of a single dose of allogeneic cells (in combination with the antagonist) has been found to be sufficient for induction of T cell tolerance to a donor tissue or organ (see Example 1). The number of cells administered may vary depending upon the type of cell used, the type of tissue or organ graft, the weight of the recipient, the general condition of the recipient and other variables known to the skilled artisan. An appropriate number of cells for use in the method of the invention can be determined by one of ordinary skill in the art by conventional methods (for example as described in Example 1). Cells are administered in a form and by a route which is suitable for induction of T cell tolerance in the recipient. Cells can be administered in a physiologically acceptable solution, such as a buffered saline solution or similar vehicle. Cells are preferably administered intravenously.

An antagonist of the invention is administered to a subject in a biologically compatible form suitable for pharmaceutical administration in vivo to induce T cell tolerance. By "biologically compatible form suitable for administration in vivo" is meant a form of the antagonist to be administered in which any toxic effects are outweighed by the therapeutic effects of the compound. The term subject is intended to include living organisms in which an immune response can be elicited, e.g., mammals. Examples of subjects include humans, dogs, cats, mice, rats, and transgenic species thereof. A gp39 antagonist of can be administered in any pharmacological form, optionally with a pharmaceutically acceptable carrier. Administration of a therapeutically active amount of the antagonist is defined as an amount effective, at dosages and for periods of time necessay to achieve the desired result (e.g., T cell tolerance). For example, a therapeutically active amount of an antagonist of gp39 may vary according to factors such as the disease state, age, sex, and weight of the individual, and the ability of the antagonist to elicit a desired response in the individual. Dosage regimens may be adjusted to provide the optimum therapeutic response. For example, several divided doses may be administered daily or the dose may be proportionally reduced as indicated by the exigencies of the therapeutic situation. As described in Example 1 for treatment with an anti-gp39 antibody, an effective treatment regimen can include initiation of antibody administration prior to tissue or organ transplantation (e.g., five to eight days before transplantation), followed by readministration of the antibody (e.g., every other day) for several weeks (e.g. two to seven weeks) after transplantation.

The active compound (e.g., an antagonist such as an antibody) may be administered in a convenient manner such as by injection (subcutaneous, intravenous, etc.), oral administration, inhalation, transdermal application, or rectal administration. Depending on the route of administration, the active compound may be coated in a material to protect the compound from the action of enzymes, acids and other natural conditions which may inactivate the compound. A preferred route of administration is by intravenous injection.

To administer an antagonist of gp39 by other than parenteral administration, it may be necessary to coat the antagonist with, or co-administer the antagonist with, a material to prevent its inactivation. For example, an antagonist can be administered to an individual in an appropriate carrier or diluent, co-administered with enzyme inhibitors or in an appropriate carrier such as liposomes. Pharmaceutically acceptable diluents include saline and aqueous buffer solutions. Enzyme inhibitors include pancreatic trypsin inhibitor, diisopropylfluorophosphate (DEP) and trasylol. Liposomes include water-in-oil-in-water emulsions as well as conventional liposomes (Strejan et al., (1984) *J. Neuroimmunol* 7:27).

The active compound may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, asorbic acid, thimerosal, and the like. In many cases, it will be preferable to include isotonic agents, for example, sugars, polyalcohols such as manitol, sorbitol, sodium chloride in the composition Prolonged absorption of the injectable compositions can be brought about by including in the composition an agent which delays absorption, for example, aluminum monostearate and gelatin.

Sterile injectable solutions can be prepared by incorporating active compound (e.g., an antagonist of gp39) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (e.g., antagonist) plus any additional desired ingredient from a previously sterile-filtered solution thereof.

When the active compound is suitably protected, as described above, the protein may be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Subsequent to or concurrent with the tolerization regimen described herein, a donor tissue or organ is transplanted into a transplant recipient by conventional techniques.

IV. Uses of the Methods of the Invention

The methods of the invention are applicable to a wide variety of tissue and organ transplant situations. The methods can be used to induce T cell tolerance in a recipient of a graft of a tissue or organ such as pancreatic islets, liver, kidney, heart, lung, skin, muscle, neuronal tissue, stomach and intestines. Thus, the methods of the invention can be applied in treatments of diseases or conditions which entail tissue or organ transplantation (e.g., liver transplantation to treat hypercholesterolemia, transplantation of muscle cells to treat muscular dystrophy, transplantation of neuronal tissue to treat Huntington's disease or Parkinson's disease etc.). In a preferred embodiment, the transplanted tissue comprises pancreatic islets. Accordingly, the invention encompasses a method for treating diabetes by pancreatic islet cell transplantation. The method comprises administering to a subject in need of treatment: 1) allogeneic or xenogeneic cells which express donor antigens, 2) an antagonist of a molecule expressed on recipient T cells which mediates contact-dependent helper effector function, such as a $gp^{39}$antagonist (e.g., anti-gp39 antibody) and 3) donor pancreatic islet cells. Preferably, the allogeneic or xenogeneic cells and the antagonist are administered to the recipient prior to administration of the pancreatic islets.

The invention is further illustrated by the following example which should not be construed as limiting. The contents of all references, patents and published patent applications cited throughout this application are hereby incorporated by reference.

EXAMPLE 1

Induction of Tolerance to Pancreatic Islet Allografts by Treatment of the Recipient with Allogeneic Cells and Anti-39

Contemporary allotransplantation studies depend on generalized immunosuppression that non-specifically ablates immune effector functions. However, immunosuppressive pharmaceuticals can cause significant side effects. In addition, allotransplantation of islet of Langerhans for the treatment of diabetes has proven refractory to this approach (see e.g. Robertson, R. P. (1992) *N. Engl. J. Med.* 327, 1861). Therapies with antibodies directed against T cells may allow successful allografting of islets in rodents, but this approach too uniformly results in generalized immunosuppression (Carpenter, C. B. (1990) *N. Engl. J. Med.* 322, 1224; Roark, J. H. et al. (1992) *Transplantation* 54, 1098; Kahan, B. D. (1992) *Curr. Opin. Immunol.* 4, 553). In this example, tolerance to islet allografts was induced in a transplant recipient by manipulating the presentation of alloantigen to T cells so as to prevent their activation. The survival of islet allografts in chemically diabetic C57BL/6 (H-$2^b$) mice was examined using the following methodology:

Induction of Diabetes

Male C57B1/6J (H-$2^b$) mice were rendered diabetic by the intravenous administration of streptozotocin (140 mg/kg). Permanent diabetes was confirmed by the demonstration of a plasma glucose concentration $\geq$400 mg/dl on three occasions over a period of one week.

Allogeneic Spleen Cell Fractionation

Donor allogeneic cells for pretreatment of graft recipients were obtained from (C57×BALB/c)(H-$2^{b/d}$)F$_1$ hybrid animals to prevent graft-versus-host disease. To isolate small lymphocytic cells, spleen cell suspensions from 8 week old (C57×BALB/c) F$_1$ female mice were depleted of erythrocytes and then size fractionated by elutriation as described in Tony, H. P. et al. (1985) *J. Exp. Med.* 161, 223; and Gosselin E. J. et al. (1988) *J. Immunol.* 140, 1408. Briefly, small lymphocytes are isolated by counterflow centrifugal elutriation, for example using a model J-6B centrifuge (Beckman Instruments, Palo Alto Calif.). Approximately 1–5×10$^8$ cells in 8 ml culture medium or balanced salt solution with 1.5% fetal bovine serum are treated with deoxyribonuclease, loaded into the elutriation chamber with a starting countercurrent flow rate of 13.5 ml/min. and spun at 4° C. at a constant speed of 3,200 rpm. A small-cell fraction with very few contaminating large cells is eluted typically at 14–19 ml/min., although the exact flow rate may depend on the medium in which the cells are suspended. In the experiments described herein, the small cell fraction was collected at 19 ml/min. (at 3,200 rpm). This fraction was completely depleted of radiation resistant (3000 rads) accessory cell function when assayed with T cell lines specific for either rabbit IgG and H$2^d$ (CDC35) or alloreactive to H$2^b$ (D10.G4). Small cells and unfractionated cells were washed twice in serum free medium before tail vein injection into allograft recipients. Approximately 40–100×10$^6$ (C57× BALB/c)F$_1$(H-$2^{b/d}$) unfractionated spleen cells or 40–100× 10$^6$ (C57×BALB/c)F$_1$(H-$2^{b/d}$) elutriated small spleen cells were used.

Pretreatment of Graft Recipients

Graft recipients were pretreated with either unfractionated (C57×BALB/c)F$_1$(H-$2^{b/d}$) allogeneic spleen cells, elutriated "fraction 19" small diameter spleen cells that had been depleted of APC activity (isolated as described above), an anti-gp39 monoclonal antibody (MR1, see Example 2, Experiment 3), or a combination of allogeneic cells and anti-gp39 antibody. The fraction 19 cells were tested at two different dose ranges, a low dosage of 40–44×10$^6$ cells or a high dose of 77–88×10$^6$ cells. Control animals received neither allogeneic cells nor antibody treatment. Allogeneic cells were administered to graft recipients by tail vein injection five to eight days prior to islet allograft transplantation. MR1 antibody treatment was at a dose of 250 μg/mouse twice weekly beginning 7 days before islet transplantation and continuing for 2–7 weeks or until graft failure. The first injection of antibody was typically given on the same day as the first injection of allogeneic spleen cells.

Islet Allograft Tranplantation

Allogeneic BALB/c (H-$2^d$) islets were isolated by a modified collagenase digestion method (Gottlieb, P. A. et al. (1990) *Diabetes* 39, 643). Islets at a dose of 30 islets/g body weight were implanted into the subrenal capsule of the recipient C57B1/6J (H-$2^b$) mice immediately after isolation. Graft survival was defined as the maintenance of a plasma glucose concentration $\leq 200$ mg/dl.

Results

In a first series of experiments, islet allograft recipients were pretreated with either allogeneic spleen cells alone or anti-gp39 antibody alone. As shown in FIG. 1, in the absence of spleen cell pretreatment, all islet allografts were rejected within 13 days of transplantation ($9\pm2$ d; range 5–13 d; N=23). Poor islet survival was also observed in animals treated only with unfractionated spleen cells containing normal APC activity ($6\pm3$ d; range 4–12 d; N=7) or low doses (40–44×$10^6$ cells) of Fraction 19 APC depleted spleen cells ($7\pm3$ d; range 3–14 d, N=16). In contrast, injection of a higher dose of Fraction 19 APC-depleted small splenocytes (75–88×$10^6$ cells) prolonged allograft survival ($19\pm10$ d; range 7–40 d; N=16). This effect on the duration of graft survival was statistically significant ($F_{3,58}=17.3$ p<0,001 when compared with groups treated with nothing, whole spleen transfusions, or the lower dose of fraction 19 spleen cells) but was not permanent. The extended but finite survival of allogeneic islets in diabetic recipients of APC depleted, fraction 19 small cells suggested that these cells alone cannot sustain allograft survival. An additional cohort of graft recipients was treated with 77–88×$10^6$ fraction 20 cells. This fraction was also composed overwhelmingly of small lymphocytes but differs from the fraction 19 population in that it contains measurable APC function. Recipients of these cells (N=6) all rejected their grafts promptly (mean= 8.5 d, range 6–12). Another group of graft recipients was treated solely with an anti-gp39 monoclonal antibody, MR1. FIG. 1 illustrates that islet allografts failed within 15 days in 7/11 mice treated only with the anti-gp39 mAb. The remaining four mice had functional grafts at the conclusion of the experiment on day 48. The results demonstrate that administration to the recipient of the MR1 anti-gp39 antibody alone can prolong islet allograft survival (mean 20=19 d; range 9 indefinite: N=5). The degree of prolongation was statistically similar to that achieved using a higher dose of Fraction 19 spleen cells alone and significantly longer than that achieved in the other three groups (p<0.05).

Figure 2A:
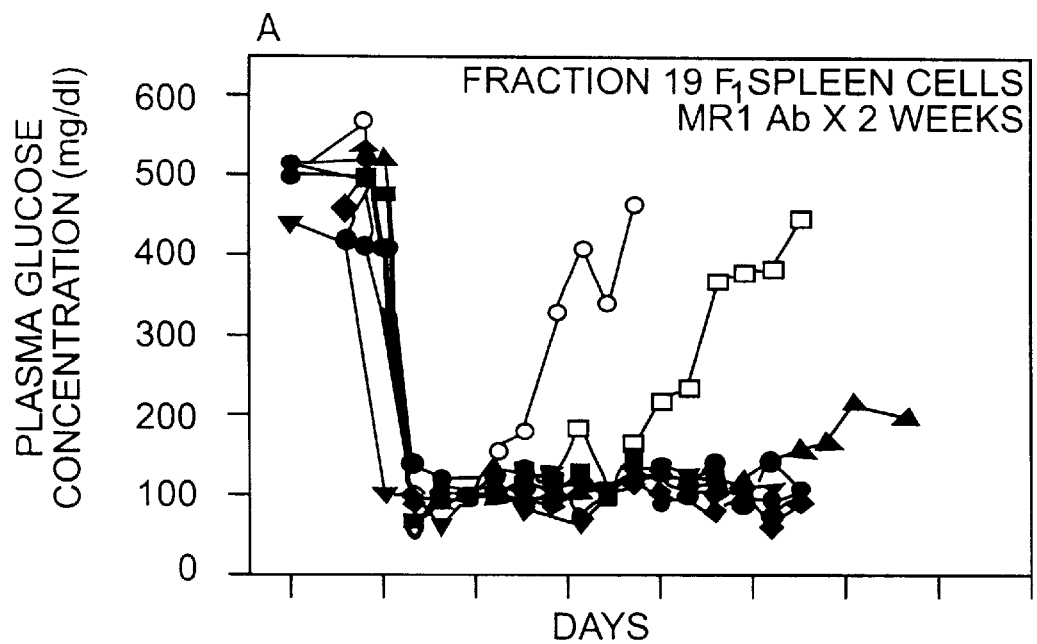
FIGS. 2A and 2B are graphic representations of the survival of transplanted pancreatic islet allografts, as measured by a decrease in plasma glucose concentration, in chemically diabetic mice pretreated with a single dose of fractionated allogeneic spleen cells together with an anti-gp39 antibody (MR1) treatment for either 2 weeks (panel A) or 7 weeks (panel B). Each curve represents data from an individual mouse. Open symbols identify recipients in which the islet allograft failed spontaneously. Closed symbols indicate mice whose islet grafts were functional at the termination of the experiment.
Figure 2B:
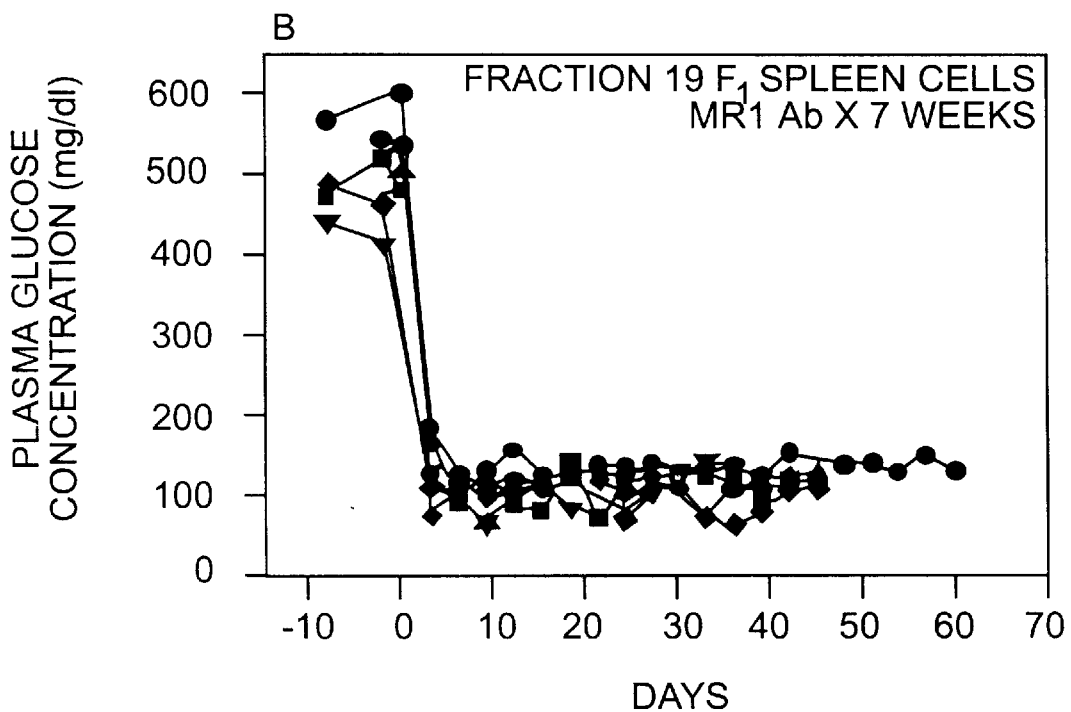

The series of experiments described above indicated that high doses of Fraction 19 APC depleted spleen cells or anti-gp39 mAb treatment alone can enhance pancreatic islet allograft survival compared to no treatment. However, neither treatment alone was effective in inducing long-term tolerance to the islet allografts in the recipients. In the next series of experiments, allogeneic spleen cell treatment was combined with anti-gp39 treatment of the recipient The combined administration of allogeneic spleen cells and anti-gp39 was found to be more effective than either reagent alone. Results are shown in FIG. 2, wherein each curve represents data from an individual mouse. Open symbols identify recipients in which the islet allograft failed spontaneously. Closed symbols indicate mice whose islet grafts were functional at the termination of the experiment. FIG. 2 (panel B), shows that indefinite graft survival was achieved in all animals treated for 7 weeks with anti-gp39 mAb and a single injection of Fraction 19 APC depleted spleen cells (N=6). Alteration of this protocol by reducing the duration of anti-gp39 treatment weakened, but did not abrogate, the favorable effect on graft survival. Indefinite graft survival was achieved in 6/8 recipients when anti-gp39 mAb was administered for only 2 weeks in combination with Fraction 19 spleen cells (FIG. 2, panel A). Indefinite graft survival was also observed in recipients treated with anti-gp39 for 2 or 7 weeks in combination with one injection of unfractionated allogeneic spleen cells.

To confirm islet graft function and the absence of insulin secretion by residual native islets not destroyed by the streptozotocin treatment, the kidneys bearing subrenal implants were removed. In all cases, unilateral nephrectomy resulted in recurrence of hyperglycemia (>300 mg/dl) within 3 days.

Islet allografts and the native pancreas were studied histologically in all animals, either when the graft failed or at the end of the experiment. Histological sections of islet allografts in the kidneys of recipients of fractionated allogeneic small lymphocytes and continuous (7 weeks) MR1 mAb treatment displayed abundant intact islets visible below the renal capsule which were devoid of mononuclear infiltration and contained well granulated insulin and glucagon positive cells. In contrast, histological sections of islet allografts in the kidneys of recipients treated with anti-gp39 mAb alone showed characteristic intense mononuclear cell inflammation and attendant islet cell destruction. In all host pancreata, islet morphology was uniformly consistent with streptozotocin diabetes.

EXAMPLE 2

Production and Characterization of Anti-gp39 Antibodies

Experiment 1—Antibodies directed against human gp39

For induction of antigen-specific T cell tolerance in a human subject, it is preferable to administer an antibody directed against human gp39. The following methodology was used to produce mouse anti-human gp39 monoclonal antibodies. Balb/c mice were immunized with a soluble gp39 fusion protein, gp39-CD8, in Complete Freund's Adjuvant (CFA). Mice were subsequently challenged 6 weeks later with soluble gp39-CD8 in Incomplete Freund's Adjuvant (IFA). Soluble gp39-CD8 was given in soluble form 4 weeks after secondary immunization. Mice were then boosted with activated human peripheral blood lymphocytes 2 weeks later, followed by a final boost with soluble gp39-CD8 after an additional 2 weeks. Splenocytes were fused with the NS-1 fusion partner on day 4 after final immunization as per standard protocols.

Clones producing anti-human gp39 antibodies were selected based on a multiple screening process. Clones were initially screened by a plate binding assay using gp39-CD8. Positive clones were then screened against a control CD8 fusion protein, CD72-CD8. Clones which scored positive on the CD8-CD72 plate binding assay were eliminated. The remaining clones were subsequently screened on resting and 6 hour activated human peripheral blood lymphocytes (PBL) by flow cytometric analysis. Hybridomas staining activated, but not resting, PBL were considered positive. Finally, the remaining clones were tested for their ability to block the binding of CD40Ig to plate bound gp39.

Approximately 300 clones were initially screened against gp39-CD8 and CD72-CD8 in the plate binding assays. Of those clones, 30 were found to detect plate-bound gp39 and not CD8. These clones were subsequently screened for detection of gp39 on activated human PBL. Approximately 15 clones detected a molecule on activated PBL, but not resting cells. Specificity was further confirmed by determining the capacity of the clones to block CD40Ig detection of plate-bound gp39. 3 of 10 clones tested block CD40Ig binding in this assay. These clones were 3E4, 2H5 and 2H8. Such clones are preferred for use in the methods described herein. Clones which tested positive on activated, but not resting PBL, were also screened for reactivity with an activated rat T cell clone, POMC8. The clone 2H8 expressed crossreactivity with this rat T cell line.

Experiment 2—Antibodies directed against human gp39

A similar immunization procedure to that described in Experiment 1 was used to produce additional antibodies directed against human gp39. One Balb/c mouse was immunized with soluble gp39-CD8 in CFA, followed by challenge with 6 hour activated human peripheral blood lymphocytes 4 weeks later. The mouse was subsequently boosted with soluble gp39-CD8 4 days prior to fusion of splenocytes with the NS-1 fusion partner per standard protocols. Screening of hybridoma clones was performed by flow cytometric staining of 6 hour activated human PBLs. Clones staining activated but not resting human PBLs were selected for subsequent analysis. Two clones, 4D9-8 and 4D9-9 were selected.

Figure 4A:
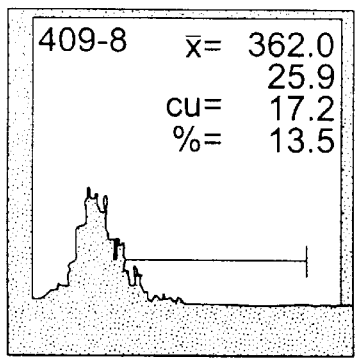
FIGS. 4A, 4B and 4C are flow cytometric profiles depicting the staining of 6 hour activated human peripheral blood lymphocytes cultured in the presence of cycloporin A stained with either mAb 4D9-8 (panel A), mAb 4D9-9 (panel B) or CD40Ig (panel C).
Figure 4B:
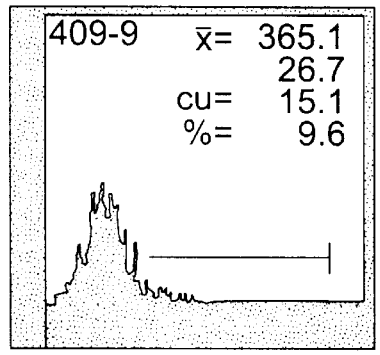
Figure 4C:
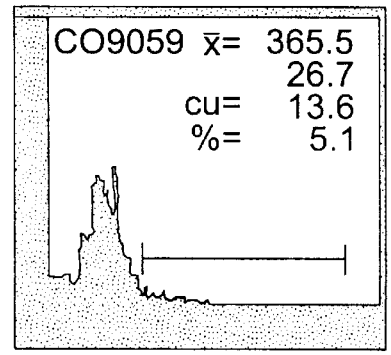
Figure 5A:
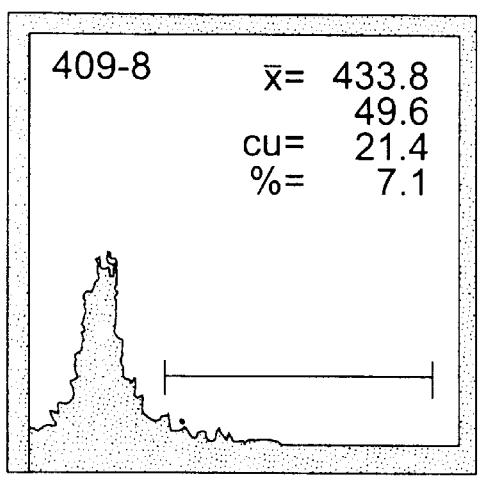
FIGS. 5A and 5B are flow cytometric profiles depicting the staining of 6 hour activated human peripheral blood lymphocytes with CD40Ig in the presence of unlabeled mAb 4D9-8 (panel A) or unlabeled mAb 4D9-9 (panel B).
Figure 5B:
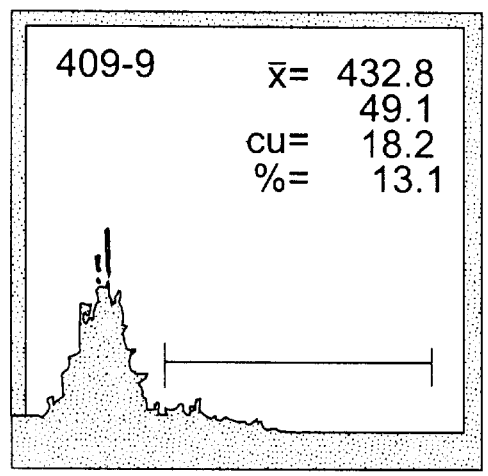

The specificity of the selected antibodies was confirmed by several assays. First, flow cytometric analysis demonstrated that 4D9-8 and 4D9-9 stain activated, but not resting peripheral blood T cells (see FIG. 3). Expression of the molecule recognized by these antibodies is detectable within 4 hours of activation, is maximal between 6–8 hours after activation, and is undetectable by 24 hours after activation. 4D9-8 and 4D9-9 recognize a molecule expressed on activated $CD3^+$PBLs, predominantly of the CD4+phenotype, but a portion of $CD8^+$ T cells also express the molecule. Expression of the molecule recognized by these mAbs is inhibited by the presence of cyclosporin A in the culture medium, as is the expression of gp39 (see FIG. 4). The kinetics and distribution of expression of the molecule recognized by these mAbs are identical to that of gp39, as detected by the fusion protein of human CD40Ig. In addition, 4D9-8 and 4D9-9 block the staining of gp39 by CD40Ig (see FIG. 5). In an ELISA assay, 4D9-8 and 4D9-9 both recognize gp39-CD8, a soluble fusion form of the gp39 molecule. Moreover, 4D9-8 and 4D9-9 both immunoprecipitate a molecule of approximately 36 kd from $^{35}$S-methionine labeled activated human PBLs. The immunoprecipitated molecule is identical to that precipitated by the human CD40Ig fusion protein.

Figure 6:
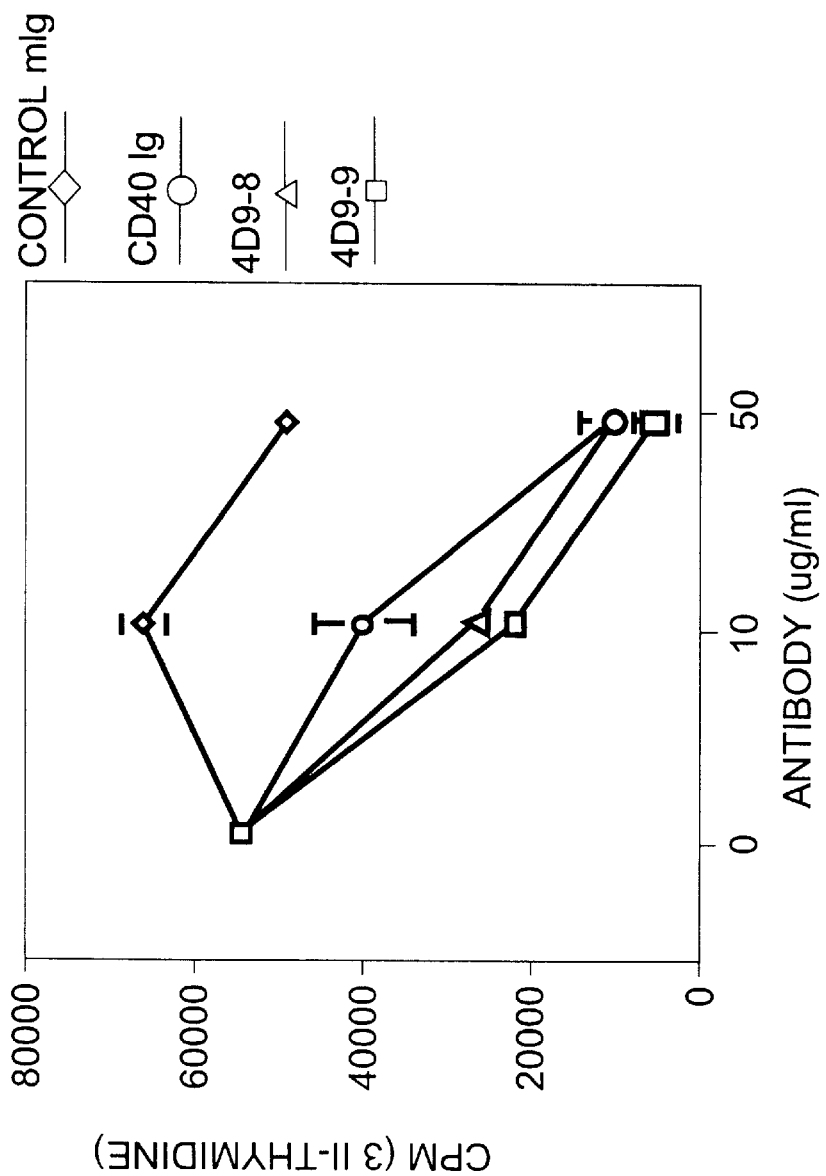
FIG. 6 is a graphic representation of the inhibition of human B cell proliferation induced by soluble gp39 and IL-4 when cultured in the presence of anti-human gp39 mAbs 4D9-8 and 4D9-9.
Figure 7:
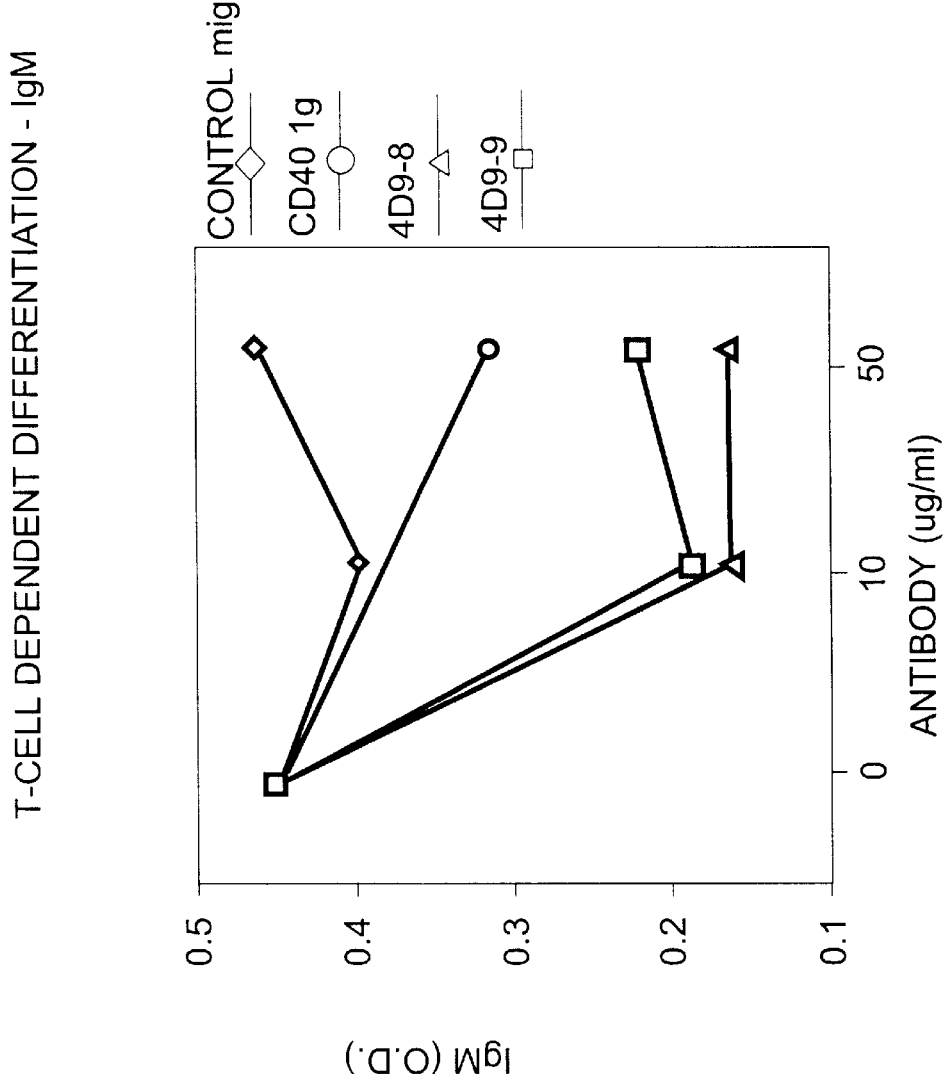
FIG. 7 is a graphic representation of the inhibition of T cell-dependent IgM production by human B cells when cultured in the presence of anti-human gp39 mAbs 4D9-8 and 4D9-9.

The functional activity of 4D9-8 and 4D9-9 was assayed as follows. First, the ability of the mAbs to inhibit the proliferation of purified human B cells cultured with IL-4 and soluble gp39 was measured. Purified human B cells were cultured with gp39 and IL-4 in the presence or absence of purified monoclonal antibodies or CD40Ig at dosages between 0 and 50 mg/ml. B cell proliferation was determined after 3 days in culture by thymidine incorporation. The results (FIG. 6) demonstrate that both 4D9-8 and 4D9-9 can inhibit B cell proliferation induced by gp39 and IL-4. Next, the ability of the mAbs to inhibit B cell differentiation, as measured by Ig production induced by anti-CD3 activated T cells and IL-2. Purified human B cells were cultured with anti-CD3 activated human T cells and IL-2 for 6 days in the presence or absence of purified monoclonal antibodies or CD40Ig as dosages between 0 and 50 mg/ml. IgM production was assessed by ELISA on day 6. The results (FIG. 7) demonstrate that both antibodies can inhibit T cell dependent B cell differentiation.

Experiment 3—Antibodies directed against mouse gp39

In one embodiment of the invention, the gp39 antagonist is an anti-mouse gp39 monoclonal antibody, MR1. The following method was used to produce the MR1 monoclonal antibody, and may be used to generate other antibodies directed toward gp39.

Hamsters were immunized intraperitoneally with 5–10$^6$ activated $T_h1$ cells (d1.6) at weekly intervals for six weeks. When the serum titer against murine $T_h1$ was greater than about 1:10,000, cell fusions were performed with polyethylene glycol using immune hamster splenocytes and NS-1. Supernatant from wells containing growing hybridomas were screened by flow cytometry on resting and activated $T_h1$. One particular hybridoma, which produced a Mab that selectively recognized activated $T_h$ was further tested and subcloned to derive MR1. MR1 was produced in ascites and purified by ion exchange HPLC. A hybridoma MR1 has been deposited with the American Type Culture Collection and assigned Accession Number HB11048.

EQUIVALENTS

Those skilled in the art will recognize, or be able to ascertain using no more than routine experimentation, many equivalents to the specific embodiments of the invention described herein. Such equivalents are intended to be encompassed by the following claims. The contents of all references and published patent applications cited throughout this application are hereby incorporated by reference.

What is claimed is:

1. A method for inducing antigen-specific T cell non-responsiveness to an antigen expressed by a transplanted cell, tissue or organ comprising administering to a host that comprises a CD40 expressing cell that expresses an antigen to which T cell non-responsiveness is to be induced in an amount of at least one gp39 antagonist selected from the group consisting of an anti-gp39 antibody or fragment thereof that specifically binds gp39, soluble CD40 and a soluble CD40 fusion protein; wherein the administered amount of such gp39 antagonist is sufficient to induce T cell non-responsiveness to said antigen.

2. The method of claim 1 wherein said antigen presenting cell is selected from the group consisting of B lymphocyte, monocyte, dendritic cell, Langerhan cell, keratinocyte, endothelial cell, astrocyte, fibroblast and a oligodendocyte.

3. The method of claim 1 wherein said antigen presenting cell is a lymphoid cell.

4. The method of claim 1 wherein the gp39 antagonist is an anti-gp39 antibody or fragment thereof.

5. The method of claim 1 wherein the antigen is an alloantigen.

6. The method of claim 1 wherein the antigen is a xenoantigen.

7. The method of claim 1 wherein the transplanted cell, tissue or organ comprises pancreatic cells, tissue or organ.

* * * * *

UNITED STATES PATENT AND TRADEMARK OFFICE
CERTIFICATE OF CORRECTION

PATENT NO. : 6,375,950 B1
DATED : April 23, 2002
INVENTOR(S) : Noelle et al.

It is certified that error appears in the above-identified patent and that said Letters Patent is hereby corrected as shown below:

<u>Title page,</u>
Item [62], Related U.S. Applications, delete "filed on Apr. 27, 1994" and insert -- filed on April 25, 1994 --

Signed and Sealed this

Sixth Day of April, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,375,950 B1
DATED : April 23, 2002
INVENTOR(S) : Randolph J. Noelle et al.

It is certified that error appears in the above-identified patent and that said Letters Patent is hereby corrected as shown below:

Title page,
Item [73], Assignee, please delete "University of Massachusetts Medical Center"

Signed and Sealed this

Third Day of August, 2004

JON W. DUDAS
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 6,375,950 B1 | Page 1 of 1 |
| APPLICATION NO. | : 09/227081 | |
| DATED | : April 23, 2002 | |
| INVENTOR(S) | : Randolph J. Noelle et al. | |

It is certified that error appears in the above-identified patent and that said Letters Patent is hereby corrected as shown below:

In the Inventors:

Please add --David C. Parker; Michael C. Appel, both of Grafton, Mass.; Nancy E. Phillips, Shrewsbury, Mass.; John P. Mordes, Newton, Mass.; Dale L. Grenier, Hubbardston, Mass.; Aldo A. Rossini, Sudbury, Mass.--

In the Assignees:

Please add --University of Massachusetts Medical Center, Worcester, Mass.--

Signed and Sealed this

Twenty-seventh Day of November, 2007

JON W. DUDAS
*Director of the United States Patent and Trademark Office*